či# (12) United States Patent
Chen (10) Patent No.: US 11,123,534 B2
(45) Date of Patent: Sep. 21, 2021

(54) NEEDLE-FREE CONNECTOR

(71) Applicant: Tai-Yi Chen, Hsinchu County (TW)

(72) Inventor: Tai-Yi Chen, Hsinchu County (TW)

( * ) Notice: Subject to any disclaimer, the term of this patent is extended or adjusted under 35 U.S.C. 154(b) by 50 days.

(21) Appl. No.: 16/398,221

(22) Filed: Apr. 29, 2019

(65) Prior Publication Data

US 2020/0129750 A1   Apr. 30, 2020

(30) Foreign Application Priority Data

Oct. 25, 2018   (TW) .................................. 107137806

(51) Int. Cl.
*A61M 39/10* (2006.01)
*A61M 5/178* (2006.01)
*A61M 39/26* (2006.01)

(52) U.S. Cl.
CPC ............ *A61M 39/10* (2013.01); *A61M 5/178* (2013.01); *A61M 2039/1038* (2013.01); *A61M 2039/1077* (2013.01); *A61M 2039/268* (2013.01)

(58) Field of Classification Search
CPC . A61M 39/10; A61M 39/26; A61M 2039/266
See application file for complete search history.

(56) References Cited

U.S. PATENT DOCUMENTS

| 3,811,803 | A  | * | 5/1974  | Frohberg | ............... | F04B 53/102 |
|           |    |   |         |          |                | 417/458     |
| 6,482,188 | B1 |   | 11/2002 | Rogers et al. | | |
| 7,160,272 | B1 | * | 1/2007  | Eyal | ....................... | A61M 39/02 |
|           |    |   |         |      |                       | 604/246 |
| 9,775,981 | B2 | * | 10/2017 | Nelson | ............. | A61B 5/150992 |
| 2006/0293629 | A1 | * | 12/2006 | Cote, Sr. | ............. | A61M 39/045 |
|           |    |   |         |           |                 | 604/246 |
| 2008/0172003 | A1 | * | 7/2008 | Plishka | ............... | A61M 39/045 |
|           |    |   |        |         |                 | 604/249 |

(Continued)

FOREIGN PATENT DOCUMENTS

| CN | 101648049 | 2/2010 |
| CN | 102448537 | 5/2012 |

(Continued)

OTHER PUBLICATIONS

Office Action of China Counterpart Application, dated Jun. 25, 2021, pp. 1-7.

*Primary Examiner* — Bhisma Mehta
*Assistant Examiner* — Neeraja Gollamudi
(74) *Attorney, Agent, or Firm* — JCIPRNET (57) ABSTRACT

A needle-free connector including a guiding base, a connecting base, a valve member, and a seal member is provided. The guiding base has a conduit, and the conduit extends downward along an axial direction. The connecting base is disposed on the guiding base and has a screw portion and a passage running through the screw portion. A chamber is formed between the guiding base and the connecting base, and the conduit and the passage respectively communicate with the chamber along the axial direction. The valve member is disposed between the guiding base and the connecting base, and is movably located in the chamber. The seal member is disposed at an end of the valve member far away from the conduit, and the seal member and the valve member are adapted to be connected into a whole in a manufacturing process.

7 Claims, 8 Drawing Sheets

(56) References Cited

U.S. PATENT DOCUMENTS

2015/0090353 A1 4/2015 Aydin
2017/0072182 A1 3/2017 Tsai et al.

FOREIGN PATENT DOCUMENTS

| CN | 102553027 | 6/2015 |
| CN | 205007360 | 2/2016 |
| CN | 210355559 | 4/2020 |
| TW | M511870 | 11/2015 |

* cited by examiner

NEEDLE-FREE CONNECTOR

CROSS-REFERENCE TO RELATED APPLICATION

This application claims the priority benefit of Taiwan application serial no. 107137806, filed on Oct. 25, 2018. The entirety of the above-mentioned patent application is hereby incorporated by reference herein and made a part of this specification.

BACKGROUND OF THE INVENTION

1. Field of the Invention

The invention relates to a connector, and in particular to a needle-free connector for medical purposes.

2. Description of Related Art

The main structure of an existing needle-free connector may be roughly divided into a housing, a sealing portion and a valve member. The sealing portion and the valve member are both arranged in the housing and are in buckled connection with each other. Since the sealing portion and the valve member are structures which are separated from each other, they need to be manufactured separately through different manufacturing processes, which leads to an increase in manufacturing cost, and the separated structures may cause unsmooth transfusion of a liquid medicine.

In addition, the valve member of the existing needle-free connector is usually made of an elastic material to prevent dust from entering a cavity of the needle-free connector and thereby causing pollution of the liquid medicine. In detail, when the needle-free connector is in an unused state, the valve member does not deform and seals an opening of the needle-free connector, and when a liquid medicine syringe penetrates into the opening of the connector and presses the valve member, the valve member elastically deforms to allow the liquid medicine to flow into the cavity from the opening.

However, the existing valve member elastically deforms integrally, and when an applied external force is insufficient, the liquid medicine may not flow into the cavity. When an applied external force is excessive, the valve member may deform irregularly, making the valve member unable to restore after the syringe is taken out.

SUMMARY OF THE INVENTION

The invention provides a needle-free connector in which a valve member and a seal member are connected into a whole in one manufacturing process to replace a separation form of an existing valve member and seal member, so as to reduce cost and solve the problem of unsmooth transfusion of a liquid medicine.

The needle-free connector of the invention is adapted to be connected to a syringe. The needle-free connector includes a guiding base, a connecting base, a valve member, and a seal member. The guiding base has a conduit. The conduit extends downward along an axial direction. The connecting base is disposed on the guiding base and has a screw portion and a passage. A chamber is formed between the guiding base and the connecting base, and the conduit and the passage respectively communicate with the chamber along the axial direction. The valve member is disposed between the guiding base and the connecting base, and is movably located in the chamber. The seal member is disposed at an end of the valve member far away from the conduit, and the seal member and the valve member are adapted to be connected into a whole in a manufacturing process.

The seal member seals the passage of the connecting base. When the syringe penetrates from the passage, the seal member is pushed to drive the valve member to generate elastic deformation, so that the seal member is displaced into the chamber to unseal the passage, and a liquid medicine is adapted to flow into the chamber through the syringe. When the syringe is separated from the passage, the valve member is adapted to drive the seal member upward move to an initial position.

Based on the above, the seal member and the valve member of the needle-free connector of the present invention are connected into a whole in one manufacturing process, so that the manufacturing process may be greatly simplified, the separation form of the existing valve member and seal member may be replaced, cost may be reduced, and the problem of unsmooth transfusion of the liquid medicine may be solved.

In addition, installation and detachment of the syringe can be easily achieved through the automatic restoration characteristic of the seal member and the valve member. The situation that when an external force is insufficient or an external force is excessively applied, the displacement of the valve member is insufficient, making the liquid medicine unable to flow into a cavity, or the valve member is irregularly deformed, making the valve member unable to be restored is avoided. Furthermore, through the automatic restoration effect of the valve member, the seal member does not need to be driven by positive and negative pressures, so that the problems of liquid medicine residual and liquid medicine backflow may be avoided.

In order to make the aforementioned objectives and advantages of the present invention comprehensible, embodiments accompanied with figures are described in detail below.

DESCRIPTION OF THE EMBODIMENTS

Figure 1A:
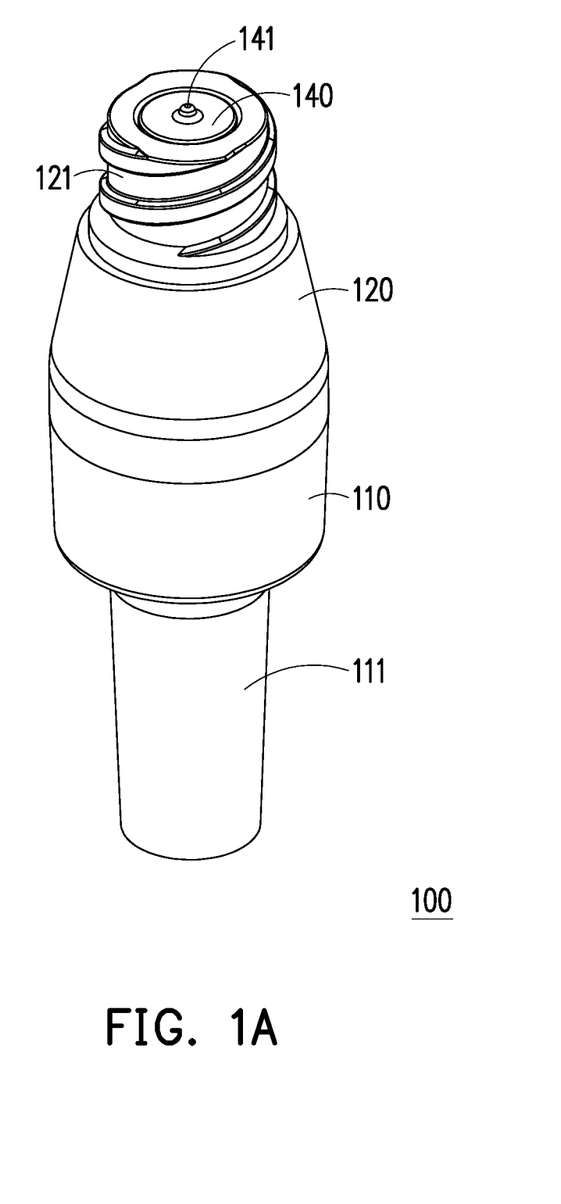
FIG. 1A is a schematic three-dimensional external view of a needle-free connector of the present invention.
Figure 1B:
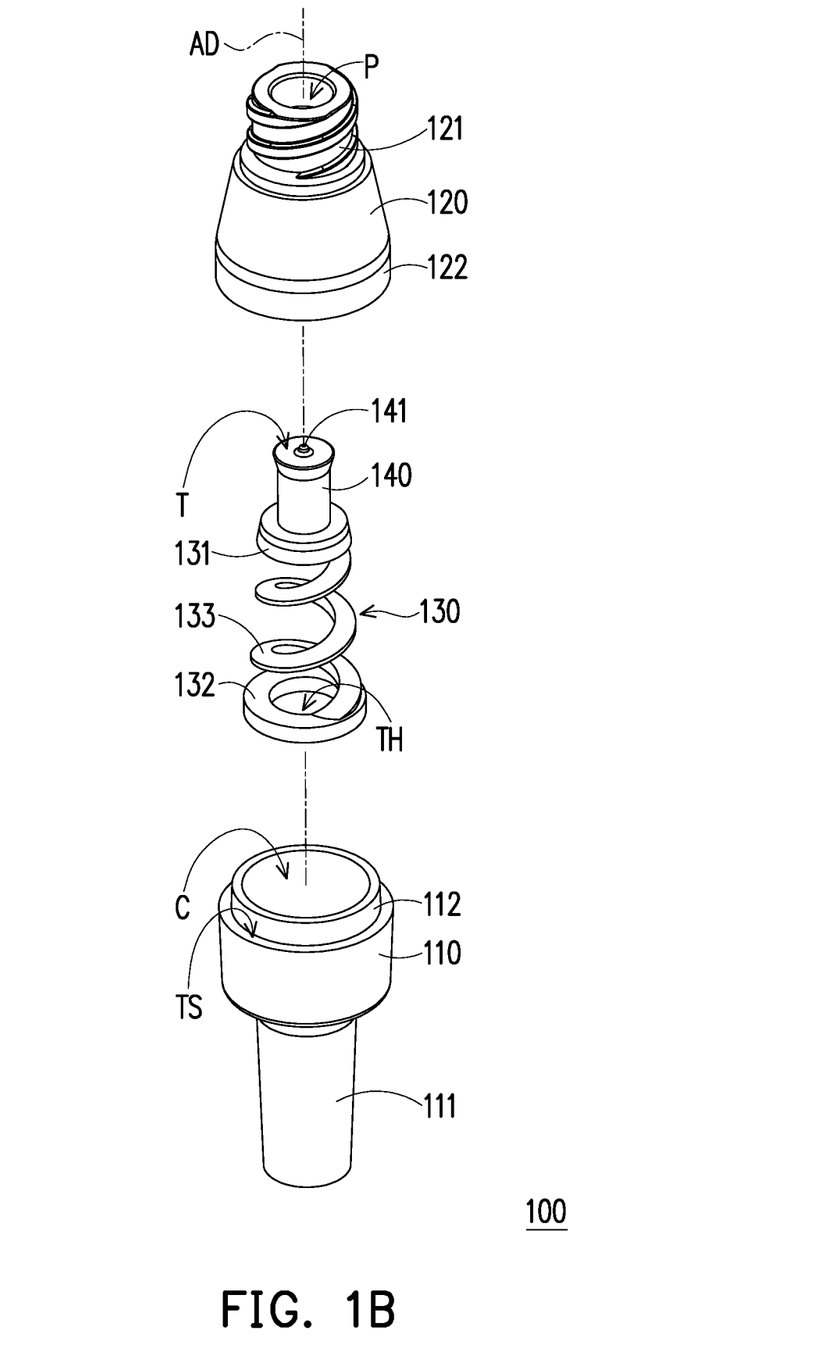
FIG. 1B is a schematic exploded view of the needle-free connector of FIG. 1A.
Figure 1C:
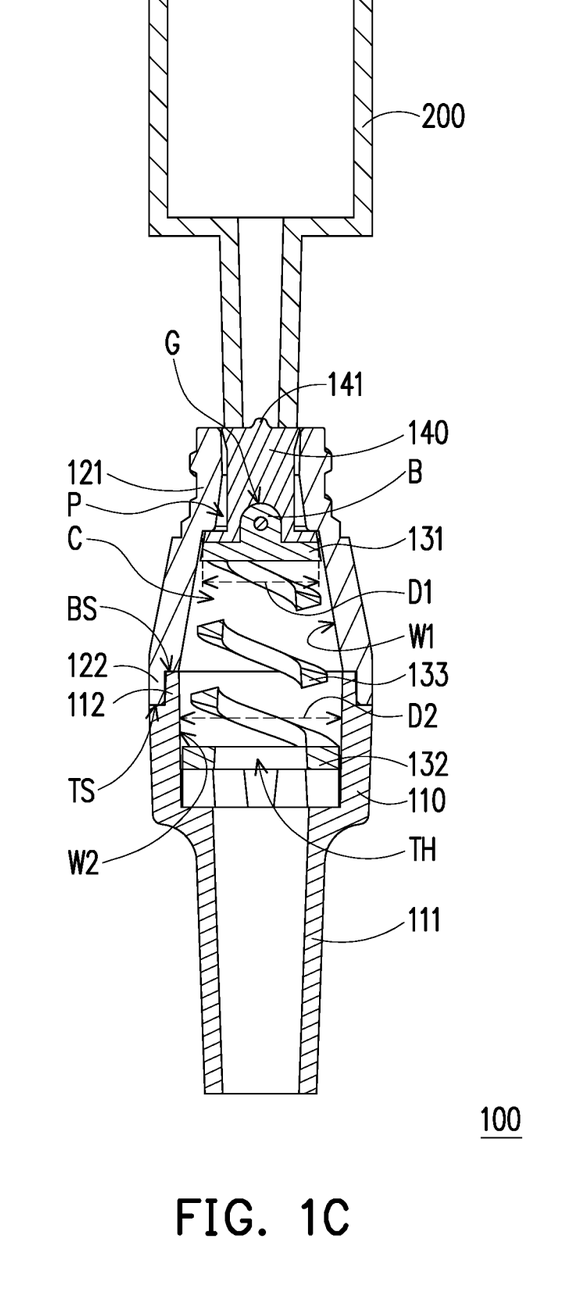
FIG. 1C is a schematic cross-sectional view of connection between a syringe and the needle-free connector of FIG. 1A.

FIG. 1A is a schematic three-dimensional external view of a needle-free connector of the present invention. FIG. 1B is a schematic exploded view of the needle-free connector of FIG. 1A. FIG. 1C is a schematic cross-sectional view of connection between a syringe and the needle-free connector of FIG. 1A.

Referring to FIG. 1A, FIG. 1B and FIG. 1C, the needle-free connector 100 of the present invention is adapted to be connected to a syringe 200, a liquid medicine enters the needle-free connector 100 through the syringe 200, and then the liquid medicine is transfused into the body of a patient through an external input tube (not shown in the figures) and an injection needle. By means of the needle-free connector 100, the injection quantity of the liquid medicine may be greatly increased, and the needle-free connector may be repeatedly used, so an existing disposable syringe may be replaced. In addition, the needle-free connector 100 may also replace a traditional syringe injection method used by medical staff to achieve needle-free injection, thereby reducing the risk of injury and infection.

The needle-free connector 100 includes a guiding base 110, a connecting base 120, a valve member 130, and a seal member 140.

The guiding base 110 has a conduit 111. The conduit 111 extends downward along an axial direction AD, and the conduit 111 is used for being connected to an external input tube (not shown in the figures). The connecting base 120 is disposed on the guiding base 110 and has a screw portion 121 and a passage P running through the screw portion 121. The screw portion 121 is adapted to be connected to the syringe 200 by means of screwing. A chamber C is formed between the guiding base 110 and the connecting base 120, and the conduit 111 and the passage P respectively communicate with the chamber C along the axial direction AD.

In addition, the guiding base 110 is a hollow member, a first engaging wall 112 is formed on a top surface TS, and the first engaging wall 112 surrounds an inner edge of the guiding base 110. The connecting base 120 is a hollow member, a second engaging wall 122 is formed on a bottom surface BS, and the second engaging wall 122 surrounds an outer edge of the connecting base 120. The outer diameter of the first engaging wall 112 corresponds to the inner diameter of the second engaging wall 122. Therefore, the first engaging wall 112 is adapted to be disposed in the second engaging wall 122 in a surface contact mode, and the guiding base 110 and the connecting base 120 are connected into a whole by a laser welding technology.

The valve member 130 is disposed between the guiding base 110 and the connecting base 120, and is movably located in the chamber C. The seal member 140 is disposed at an end of the valve member 130 far away from the conduit 111, and the seal member and the valve member are adapted to be connected into a whole in a manufacturing process. In the present embodiment, the valve member 130 and the seal member 140 may be connected into a whole in a physical mode or a chemical mode, the physical mode is structural clamping combination, and the chemical mode is adhesion connection of materials or self-bonding of materials.

Figure 1D:
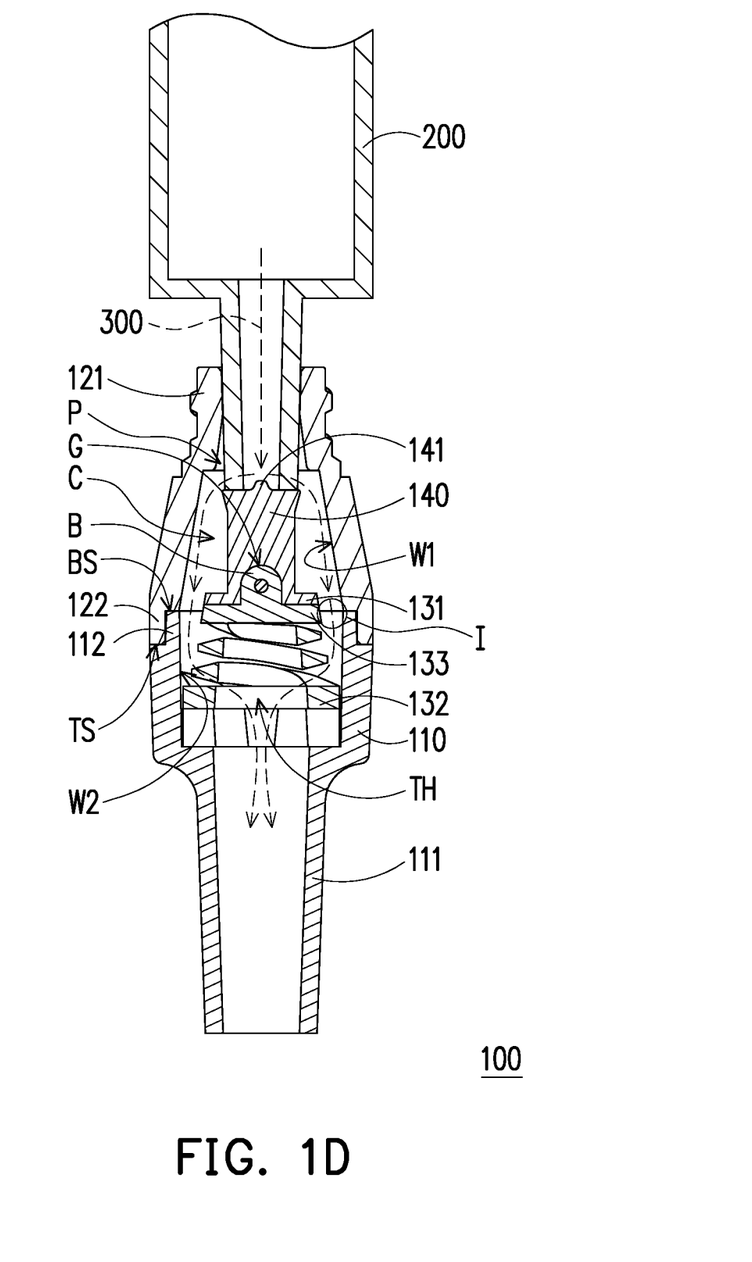
FIG. 1D is a schematic cross-sectional view showing a liquid medicine flowing into the needle-free connector of FIG. 1A.

FIG. 1D is a schematic cross-sectional view showing a liquid medicine flowing into the needle-free connector of FIG. 1A.

Referring to both FIG. 1C and FIG. 1D, in an initial state, the seal member 140 seals the passage P of the connecting base 120. When the syringe 200 penetrates from the passage P of the connecting base 120, the seal member 140 is pushed by the syringe 200 to drive the valve member 130 to move downward, so that the seal member 140 is displaced into the chamber C to unseal the passage P. A liquid medicine 300 is adapted to flow into the chamber C through the syringe 200.

When the syringe 200 is separated from the passage P of the connecting base 120, the valve member 130 is adapted to drive the seal member 140 to upward move to an initial position to re-seal the passage P. In short, the valve member 130 is suitably for elastically deform after being pushed by an external force (syringe 200), so that the valve member 130 may move up and down in the chamber C to eliminate the sealed state of the connecting base 120.

Referring to FIG. 1B to FIG. 1C. In detail, the valve member 130 includes a support portion 131, a flow-through portion 132, and an elastic portion 133.

The support portion 131 is disposed in the connecting base 120 and is connected to the seal member 140. Further, the support portion 131 has a locking block B, the seal member 140 has a groove G, and the locking block B is disposed in the groove G to connect the support portion 131 and the seal member 140 into a whole. In other embodiments, the support portion and the seal member may also be connected into a whole by means of adhesion.

The flow-through portion 132 is disposed in the guiding base 110 and has a through hole TH, and the through hole TH is aligned with and communicates with the conduit 111. This shows that after entering the chamber C, the liquid medicine 300 flows through the through hole TH and the conduit 111 in sequence, and flows out of the guiding base 110.

The elastic portion 133 is disposed between the support portion 131 and the flow-through portion 132. The elastic portion 133 is a compression elastic member. This shows that the elastic portion 133 is preset to be in a stretched state and is adapted to pushing outward the support portion 131 and the flow-through portion 132. In this way, when the elastic portion 133 is subjected to an external force, a compression phenomenon will occur and elastic force will be accumulated. After the external force is removed, the support portion 131 and the seal member 140 are driven upward to initial positions by releasing the accumulated elastic force.

Referring to FIG. 1B to FIG. 1D, the seal member 140 has a water breaking portion 141 disposed on a top surface T of the seal member 140 facing the passage P. In the present embodiment, the water breaking portion 141 includes a lug protruding upward in the axial direction AD from a center of the top surface T. Here, the lug is higher than the top surface T of the seal member 140, which may prevent some of the liquid medicine 300 from accumulating on the top surface T of the seal member 140, thereby solving the pollution problem of the liquid medicine.

Referring to FIG. 1C to FIG. 1D, the connecting base 120 has a first inner ring surface W1, and the inner diameter D1 of the first inner ring surface W1 gradually increases toward the conduit 111.

When the syringe 200 is not installed in the needle-free connector 100, the seal member 140 engages with and seals the passage P of the airtight connecting base 120, and the outer diameter of the support portion 131 is closely fitted to one end of the first inner ring surface W1 adjacent to the screw portion 121, where the end of the first inner ring surface W1 adjacent to the screw portion 121 has the smallest inner diameter D1. When the needle-free connector 100 is installed with the syringe 200, the seal member 140 and the support portion 131 are pushed by an external force to move downward. In this way, the seal member 140 gets away from the passage P of the connecting base 120, and a gap I is generated between the support portion 131 and the first inner ring surface W1, thereby forming a flow path of the liquid medicine 300.

The guiding base 110 has a second inner ring surface W2, and the inner diameter D2 of the second inner ring surface is equidistantly arranged. The outer diameter of the flow-through portion 132 is closely fitted to the inner diameter D2 of the second inner ring surface W2, so that the flow-through portion 132 is fixed in the chamber C.

Figure 2A:
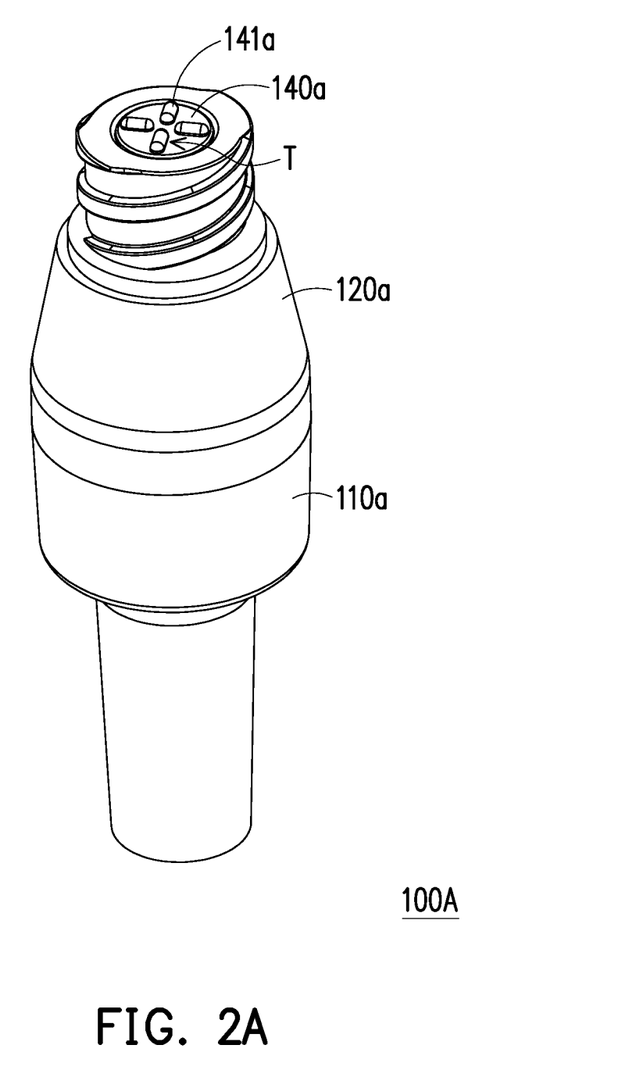
FIG. 2A is a schematic three-dimensional external view of a needle-free connector of another embodiment of the present invention.
Figure 2B:
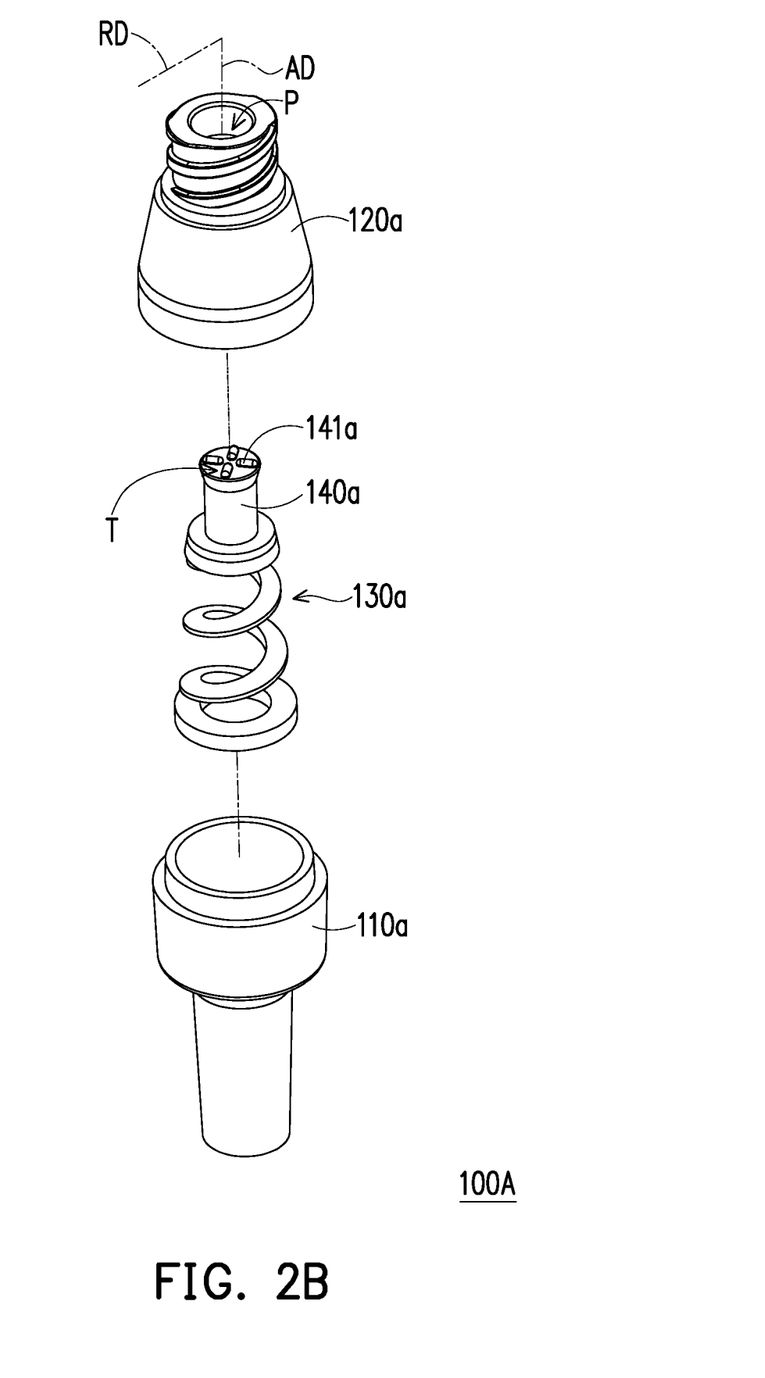
FIG. 2B is a schematic exploded view of the needle-free connector of FIG. 2A.

FIG. 2A is a schematic three-dimensional external view of a needle-free connector of another embodiment of the present invention. FIG. 2B is a schematic exploded view of the needle-free connector of FIG. 2A.

Referring to FIG. 2A, FIG. 2B and FIG. 1D, a needle-free connector 100A of the present embodiment is similar to the needle-free connector 100 of FIG. 1A, except that a water-breaking portion 141a of a seal member 140a includes a plurality of arc-shaped blocks (for example, four arc-shaped blocks in the figures), which are respectively disposed on a top surface T and extend outward along a radial direction RD. The plurality of arc-shaped blocks have a height drop relative to the top surface T, which may prevent some of the liquid medicine 300 from accumulating on the top surface T of the seal member 140a due to surface tension, thereby solving the residual problem of the liquid medicine 300. Furthermore, the plurality of arc-shaped blocks are spaced from one another, thereby forming a plurality of gaps for the liquid medicine 300 to flow, and also improving the flowing smoothness of the liquid medicine 300 from the syringe 200 into the needle-free connector 100.

Additionally, in the present embodiment, the plurality of arc-shaped blocks are, for example, silicone, rubber, plastic or other similar materials, depending on the required specification of the needle-free connector.

Figure 3A:
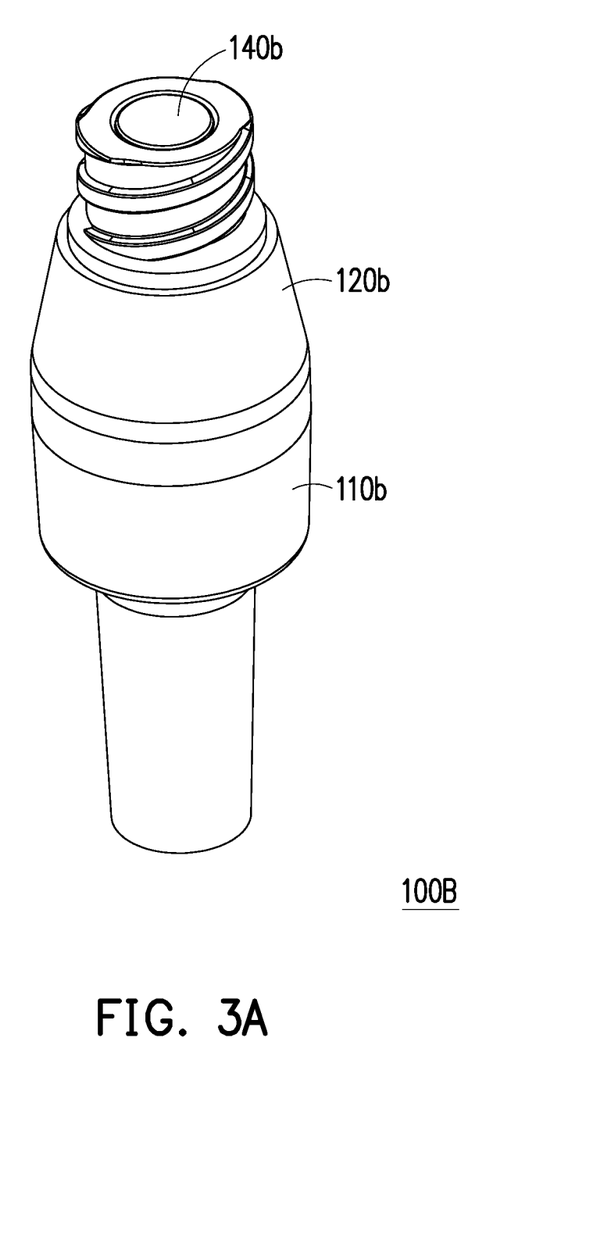
FIG. 3A is a schematic three-dimensional external view of a needle-free connector of yet another embodiment of the present invention.
Figure 3B:
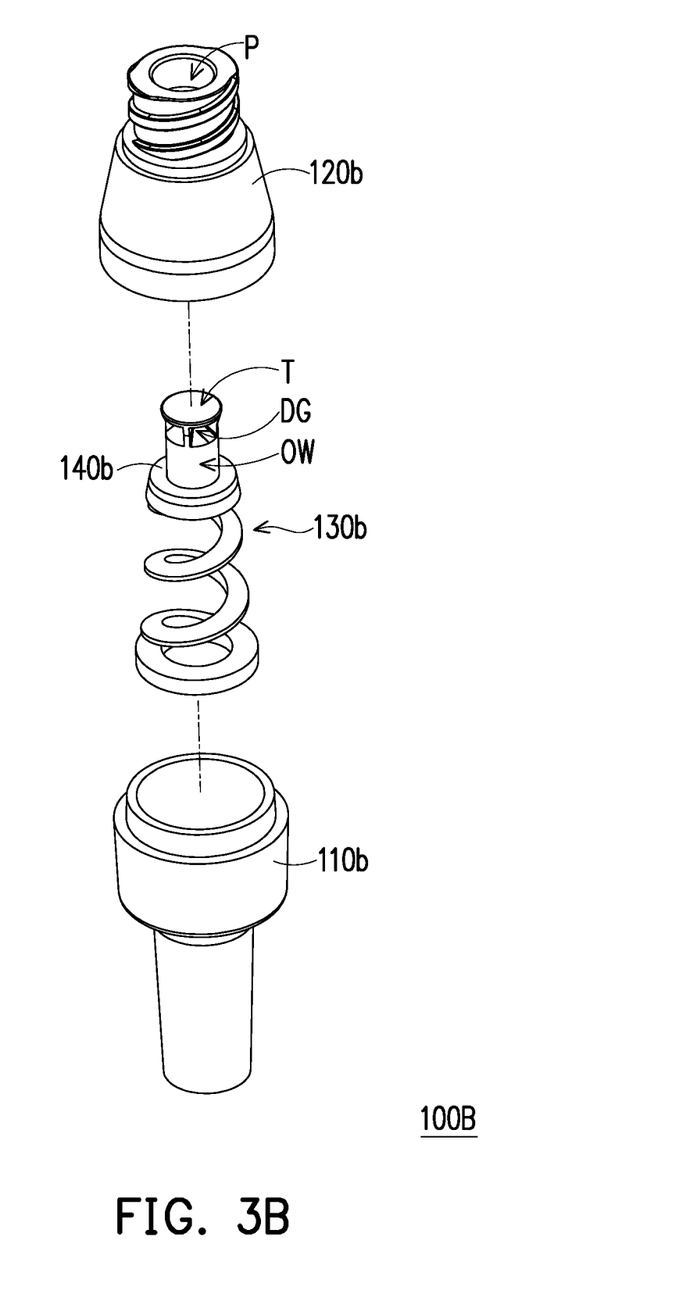
FIG. 3B is a schematic exploded view of the needle-free connector of FIG. 3A.

FIG. 3A is a schematic three-dimensional external view of a needle-free connector of yet another embodiment of the present invention. FIG. 3B is a schematic exploded view of the needle-free connector of FIG. 3A.

Referring to FIG. 3A, FIG. 3B and FIG. 1B, the needle-free connector 100B of the present embodiment is similar to the needle-free connector 100 of FIG. 1A, except that a seal member 140b has a plurality of deformation grooves DG formed in an outer ring wall OW of the seal member 140b at intervals. Further, referring to both FIG. 1C and FIG. 1D, the plurality of deformation grooves DG may improve the elasticity of a top surface T of the seal member 140b. When the top surface T is pressed down by the syringe 200, the top surface T will elastically deform, so that the liquid medicine 300 may flow into the chamber C from a gap between the top surface T and the syringe 200. When the syringe 200 no longer presses down the top surface T, the seal member 140b will elastically restore to make the top surface T restore to a flat surface. Therefore, the plurality of deformation grooves DG may improve the flowing smoothness of the liquid medicine 300 from the syringe 200 into the needle-free connector 100.

Based on the above, the seal member and the valve member of the needle-free connector are connected into a whole in one manufacturing process, so that the manufacturing process may be greatly simplified, the separation form of the existing valve member and seal member may be replaced, cost may be reduced, and the problem of unsmooth transfusion of the liquid medicine may be solved.

In addition, installation and detachment of the syringe may be easily achieved through the automatic restoration characteristic of the valve member. In detail, the valve member has the elastic portion to facilitate linear deformation. When a user installs the syringe, the elastic portion elastically deforms easily, which may avoid the situation that the liquid medicine cannot flow into a cavity due to insufficient displacement of the valve member. When the user removes the syringe, the elastic portion may restore through the release of the elastic force thereof, thus avoiding the situation that the valve member cannot be restored due to irregular deformation. Furthermore, by the automatic restoration effect of the valve member, the seal member does not need to be driven by positive and negative pressures, so that the problems of liquid medicine residual and liquid medicine backflow can be avoided.

Although the present invention has been disclosed as above by the embodiments, they are not intended to limit the present invention. Any person of ordinary skill in the art can make some changes and modifications without departing from the spirit and scope of the present invention. Therefore, the scope of protection of the present invention is subject to the scope of the appended claims.

What is claimed is:

1. A needle-free connector adapted to be connected to a syringe, the needle-free connector comprising:
   a guiding base comprising a conduit, the conduit extending downward along an axial direction;
   a connecting base disposed on the guiding base and comprising a screw portion and a passage running through the screw portion, a chamber being formed between the guiding base and the connecting base, and the conduit and the passage respectively communicating with the chamber along the axial direction;
   a valve member disposed between the guiding base and the connecting base and movably located in the chamber; and
   a seal member disposed at an end of the valve member far away from the conduit, the seal member and the valve member adapted to be formed as a single piece in a manufacturing process, wherein, the seal member has a water breaking portion disposed on a top surface facing the passage of the connecting base, the syringe is in contact with the top surface of the seal member and surrounds the water breaking portion,
   wherein the seal member is used for sealing the passage of the connecting base, when the syringe penetrates from the passage, the seal member is pushed to drive the valve member to move downward, so that the seal member is displaced into the chamber to unseal the passage, a liquid medicine is adapted to flow into the chamber through the syringe, and when the syringe is separated from the passage, the valve member is adapted to drive the seal member to upward move to an initial position;
   wherein, the valve member comprises a support portion, a flow-through portion, and an elastic portion, the support portion is disposed in the connecting base and is connected to the seal member, the flow-through portion is disposed in the guiding base and is aligned with the conduit, the elastic portion is disposed between the support portion and the flow-through portion, and the elastic portion is adapted to outward push the support portion and the flow-through portion;
   wherein, the support portion has a locking block, the seal member has a groove, and the locking block is disposed in the groove to connect the support portion and the seal member.

2. The needle-free connector according to claim 1, wherein the water breaking portion comprises a lug protruding upward along the axial direction from a center of the top surface.

3. The needle-free connector according to claim 1, wherein the support portion and the seal member are formed as a single piece.

4. The needle-free connector according to claim 1, wherein the connecting base comprises a first inner ring surface, and an inner diameter of the first inner ring surface gradually increases toward the conduit.

5. The needle-free connector according to claim 1, wherein the guiding base comprises a second inner ring surface, and an inner diameter of the second inner ring surface is equidistantly arranged.

6. The needle-free connector according to claim 1, wherein the water breaking portion comprises a plurality of arc-shaped blocks which are respectively disposed on the top surface and extend outward along a radial direction.

7. The needle-free connector according to claim 1, wherein the seal member has a plurality of deformation grooves formed in an outer ring wall of the seal member at intervals.

* * * * *